(12) United States Patent
Christophersen et al.

(10) Patent No.: US 11,274,280 B2
(45) Date of Patent: Mar. 15, 2022

(54) GENERATION OF FUNCTIONAL BETA CELLS FROM HUMAN PLURIPOTENT STEM CELL-DERIVED ENDOCRINE PROGENITORS

(71) Applicant: Novo Nordisk A/S, Bagsvaerd (DK)

(72) Inventors: Nicolaj Stroeyer Christophersen, Virum (DK); Ulrik Doehn, Oelstykke (DK); Mattias Hansson, Malmoe (SE)

(73) Assignee: Novo Nordisk A/S, Bagsvaerd (DK)

( * ) Notice: Subject to any disclaimer, the term of this patent is extended or adjusted under 35 U.S.C. 154(b) by 387 days.

(21) Appl. No.: 16/078,763

(22) PCT Filed: Feb. 24, 2017

(86) PCT No.: PCT/EP2017/054390
§ 371 (c)(1),
(2) Date: Aug. 22, 2018

(87) PCT Pub. No.: WO2017/144695
PCT Pub. Date: Aug. 31, 2017

(65) Prior Publication Data
US 2019/0085295 A1    Mar. 21, 2019

(30) Foreign Application Priority Data
Feb. 24, 2016  (EP) .................................... 16157181

(51) Int. Cl.
*C12N 5/071*  (2010.01)
*C12N 5/074*  (2010.01)

(52) U.S. Cl.
CPC ......... *C12N 5/0676* (2013.01); *C12N 5/0696* (2013.01); *C12N 2501/01* (2013.01); *C12N 2501/15* (2013.01); *C12N 2501/72* (2013.01); *C12N 2501/845* (2013.01); *C12N 2501/91* (2013.01)

(58) Field of Classification Search
CPC .................................................. C12N 5/0676
See application file for complete search history.

(56) References Cited

U.S. PATENT DOCUMENTS

| | | |
|---|---|---|
| 9,150,833 B2 | 10/2015 | Xu |
| 10,138,465 B2 | 11/2018 | Rezania |
| 2014/0315301 A1 | 10/2014 | Hanna et al. |
| 2014/0329315 A1 | 11/2014 | Odorico et al. |
| 2015/0240235 A1 | 8/2015 | Collombat et al. |
| 2015/0250824 A1* | 9/2015 | Ma .......................... A61K 35/34 424/93.7 |
| 2015/0329828 A1 | 11/2015 | Rezania |
| 2015/0368616 A1 | 12/2015 | Jensen et al. |
| 2021/0230554 A1 | 7/2021 | Christophersen et al. |

FOREIGN PATENT DOCUMENTS

| | | | |
|---|---|---|---|
| JP | 2016503654 A | 2/2016 | |
| WO | 2011143299 A2 | 11/2011 | |
| WO | 2012175633 A1 | 12/2012 | |
| WO | 2013/163739 A1 | 11/2013 | |
| WO | WO-2013163739 A1 * | 11/2013 | ............. A61P 43/00 |
| WO | 2014/033322 A1 | 3/2014 | |
| WO | WO-2014201167 A1 * | 12/2014 | ................ A61P 5/50 |
| WO | 15002724 A2 | 1/2015 | |
| WO | 15028614 A1 | 3/2015 | |
| WO | WO-2015028614 A1 * | 3/2015 | ........... C12N 5/0613 |
| WO | 2017144695 A1 | 8/2017 | |

OTHER PUBLICATIONS

Xu et al. 2014, Embo J., vol. 33(19), pp. 2157-2170) (Year: 2014).*
Purwana et al. (2014, Diabetes, vol. 63, pp. 4197-4205) (Year: 2014).*
Aguayo-Mazzucato et al "Stem cell therapy for type 1 diabetes mellitus" Nature Reviews Endocrinology 2010 vol. 6 Issue 3 pp. 139-148.
Bruin et al "Characterization of polyhormonal insulin-producing cells derived in vitro from human embryonic stem cells" Stem Cell Research 2014 vol. 12 No. 1 pp. 194-208.
D'Amour "Production of pancreatic hormone-expressing endocrine cells from human embryonic stem cells" Nature Biotechnology 2006 vol. 24 No. 11 pp. 1392-1401.
Halban et al "Gene and Cell-Replacement Therapy in the treatment of Type 1 Diabetes" Diabetes 2001 vol. 50 No. 10 pp. 2181-2191.
Nostro et al "Generation of beta cells from human pluripotent stem cells: Potential for regenerative medicine" Seminars in Cell & Developmental Biology 2012 vol. 23 Issue 6 pp. 701-710.
Nostro et al "Stage-specific signaling through TGFBeta family members and WNT regulates patterning and pancreatic specification of human pluripotent stem cells" Development 2011 vol. 138 No. 5 pp. 861-871.
Pagliuca et al "Generation of Function Human Pancreatic Beta Cells in vitro" Cell 2014 vol. 159 No. 2 pp. 428-439 doi:10.1016/j.cell.2014.09.040.
Rezania et al; Reversal of Diabetes With Insulin-Producing Cells Derived in Vitro From Human Pluripotent Stem Cells;Nature Biotechnology 32, 1121-1133 (2014) doi:10.1038/nbt.3033.
Schiesser et al "Generation of Beta cells from Human Pluripotent Stem Cells: Are we there yet?" Annals of the New York Academy of Sciences 2014 vol. 1311 No. 1 pp. 124-137.
Shapiro, J. A. M. et al. "Islet Transplantation in seven patients with type 1 diabetes mellitus using a glucocorticoid-free immunosuppressive regimen" New England Journal of Medicine 2000 vol. 343 No. 4 pp. 230-238.
Pagliuca et al., "Generation of Functional Human Pancreatic ? Cells In Vitro," Cell, 2014, vol. 159, No. 2, pp. 428-139.
Rezania et al., "Reversal of diabetes with insulin-producing cells derived in vitro from human pluripotent stem cells," Nature Biotechnology, 2014, vol. 32, No. 11, pp. 1121-1133.

\* cited by examiner

*Primary Examiner* — Thaian N. Ton
*Assistant Examiner* — David A Montanari
(74) *Attorney, Agent, or Firm* — Leon Lum

(57) ABSTRACT

The present invention relates to generation of functional beta cells from human pluripotent stem cell-derived endocrine progenitors. The present invention also relates to functional beta cells produced by said methods and uses of said beta cells.

14 Claims, 15 Drawing Sheets

A.

B.

A.

BC step1 protocol: 100% (Q2)

B.

BC step1 protocol+DAPT: 270% (Q2)

C. BC step1 protocol+dbcAMP: 165% (Q2)

BC step 1: DZNEP 1uM + Alk5i 10 uM + 10 ug/ml Heparin + 10 mM Nicotinamide

A.

B.

BC step 1: DZNEP 1uM + Alk5i 10 uM + 10 ug/ml Heparin + 10 mM Nicotinamide

BC step 1 method: DZNEP 1uM + Alk5i 10 uM + 10 ug/ml Heparin
+ 10 mM Nicotinamide
BC step 2 method: 12% KOSR

A.

B.

GENERATION OF FUNCTIONAL BETA CELLS FROM HUMAN PLURIPOTENT STEM CELL-DERIVED ENDOCRINE PROGENITORS

CROSS-REFERENCE TO RELATED APPLICATIONS

This application is a 35 U.S.C. § 371 National Stage application of International Application PCT/EP2017/054390 (WO 2017/144695), filed Feb. 24, 2017, which claims priority to European Patent Application 16157181.5, filed Feb. 24, 2016; the contents of which are incorporated herein by reference.

TECHNICAL FIELD

The present invention relates to methods of generating functional mature beta cells from human pluripotent stem cells derived endocrine progenitors.

BACKGROUND

Islet cell transplantation has been used to treat type 1 diabetic patients showing superior glucose homeostasis compared with insulin therapy but this therapy is limited by organ donations. Human Pluripotent stem cells (hPSCs) such as human embryonic stem cells (hESCs) can proliferate infinitively and differentiate into many cell types, including beta cells (BCs) and may address the shortage of donor islets. Protocols to differentiate hPSC into definitive endoderm, (DE), pancreatic endoderm (PE) cells and endocrine progenitors (EP) in vitro have been provided in WO2012/175633, WO 2014/033322 and WO2015/028614 respectively. It is challenging to make glucose-responsive insulin-secreting BCs in vitro from hPSCs. Most protocols result in insulin-producing cells that fail to recapitulate the phenotype of BCs as they also co-express other hormones such as glucagon and are unresponsive to glucose stimulation.

Rezania, A. et al. "Reversal of diabetes with insulin-producing cells derived in vitro from human pluripotent stem cells" Nature Biotechnology 32, 1121-1133 (2014) and Pagliuca, F. W. et al. "Generation of Functional Human Pancreatic b Cells In Vitro" Cell 159(2), 428-439, Oct. 9, 2014, reported the in vitro differentiation of hESCs into insulin-secreting cells. Using static incubation studies, cells from both groups were sensitive to glucose stimulation showing approximately 2-fold increase in insulin output after glucose stimulation. This response varied however qualitatively and quantitatively from that of primary adult beta cells. As comparison, human islet stimulation index is reported to be two to ten or higher (Shapiro, J. A. M. et al. "Islet Transplantation in seven patients with type 1 diabetes mellitus using a glucocorticoid-free immunosuppressive regimen" New England Journal of Medicine 343, 230-238, July 27 (2000).

The reported stem cell-derived BCs also failed to display insulin response to glucose in a dynamic cell perfusion assay and are thus functionally immature relative to primary human BCs.

Efficient protocol for making functional mature BCs from hPSC-derived endocrine progenitors that can respond to glucose in a dynamic cell perfusion assay is not known. It is critical to improve current protocols to generate fully functional mature BCs for a more consistent cell product similar to human islets to obtain a predictable outcome following transplantation as well as for screening purposes in vitro.

SUMMARY

The present invention relates to improved methods for generation of functional mature beta cells from human pluripotent stem cell-derived endocrine progenitors. The present invention also relates to glucose responsive fully differentiated beta-cells. The present invention further relates to functional mature beta cells obtainable by the methods of the present invention. The present invention further relates to medical use of said cells inter alia in the treatment of type I diabetes. The present invention may also solve further problems that will be apparent from the disclosure of the exemplary embodiments.

DESCRIPTION

Figure 1:
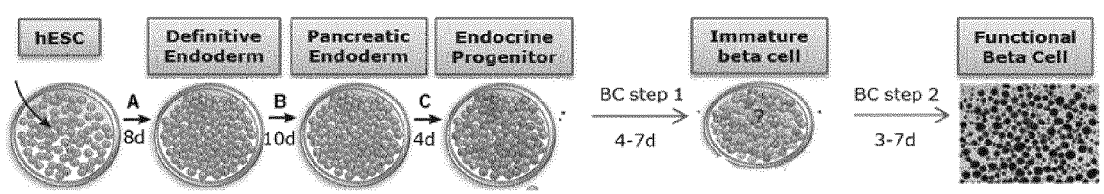
FIG. 1 shows the screening approach where undifferentiated human embryonic stem cells (hESCs) were differentiated into Definitive Endoderm (DE) and reseeded in T75 flasks, where the cells were further differentiated into Pancreatic Endoderm (PE) and Endocrine Progenitor (EP). The Beta cells (BC) step 1 screen was started at the EP stage and continued for 4-7 days, and analysed by qICC monitoring and/or flow cytometry of NKX6.1+/INS+/GCG− cell number. BC step 2 screen was started at the end of BC step 1 screen and continued for 3-7 day period in 3D suspension cultures by dissociating to single cells at the end of BC step 1 and re-aggregation to clusters on orbital shaker at 50 rpm. Cells were analysed by static and/or dynamic GSIS, INS protein content, ICC, and qPCR.

The inventors of the present invention have performed extensive small-molecule screens and identified a novel and simple two-step method that generates functional mature Beta cells (BC) from the human pluripotent stem cell-derived endocrine progenitor stage. The first step of the protocol (BC step 1) induces high fraction of INS+ and NKX6.1+ double positive cells and only few GCG positive cells. The second step of the protocol (BC step 2) generates functional mature BC that respond strongly to repeated glucose challenges in vitro. Importantly, the hPSC-derived BC cells respond to repeated glucose+/−Exendin4 challenges in a dynamic perfusion assay. The resulting functional mature BC also respond to increased glucose levels in vivo 3 weeks after transplantation to the kidney capsule of non-diabetic mice.

The inventors of the present invention have found that gamma-Aminobutyric acid (GABA) administration in vivo following cell transplantation can potentially potentiate functional effect of transplanted BC. The resulting fully functional BC population can be used as an in vitro-based BC product to study human BC function, screening compounds for regulating insulin secretion, insulin protein processing, insulin secretion and—mechanism, GSIS studies, calcium influx signaling, autoimmune BC destruction, and BC trans differentiation. Throughout this application terms method or protocol or process may be used interchangeably.

Particular Embodiments

1. A method for generation of functional mature beta cells from human pluripotent stem cell-derived endocrine progenitors comprising the steps of (1) culturing the stem cell-derived endocrine progenitor cells in a medium comprising histone methyltransferase EZH2 inhibitor, transforming growth factor beta (TGF)-beta signaling pathway inhibitor, Heparin and Nicotinamide in basal medium, to obtain INS+ and NKX6.1+ double positive immature beta cells and (2) culturing the beta cells obtained in step (1) with 12% KOSR and GABA, to obtain functional mature beta cells.

2. The method for generation of functional mature beta cells from human pluripotent stem cell-derived endocrine progenitors according to embodiment 1, wherein histone methyltransferase EZH2 inhibitor is 3-Deazaneplanocin A (DZNep).

3. The method for generation of functional mature beta cells from human pluripotent stem cell-derived endocrine progenitors according to embodiment 2, wherein concentration of DZNep is below 1 µM.

4. The method for generation of functional mature beta cells from human pluripotent stem cell-derived endocrine progenitors according to embodiment 2, wherein concentration of DZNep is 1 µM.

5. The method for generation of functional mature beta cells from human pluripotent stem cell-derived endocrine progenitors according to embodiment 2, wherein concentration of DZNep is in a range of 1-10 µM.

6. The method for generation of functional mature beta cells from human pluripotent stem cell-derived endocrine progenitors according to embodiment 2, wherein concentration of DZNep is 10 µM.

7. The method for generation of functional mature beta cells from human pluripotent stem cell-derived endocrine progenitors according to embodiment 1, wherein transforming growth factor beta (TGF)-beta signaling pathway inhibitor is Alk5iII.

8. The method for generation of functional mature beta cells from human pluripotent stem cell-derived endocrine progenitors according to embodiment 7, wherein concentration of Alk5iII is below 1 µM.

9. The method for generation of functional mature beta cells from human pluripotent stem cell-derived endocrine progenitors according to embodiment 7, wherein concentration of Alk5iII is 1 µM.

10. The method for generation of functional mature beta cells from human pluripotent stem cell-derived endocrine progenitors according to embodiment 7, wherein concentration of Alk5iII is in a range of 1-10 µM.

11. The method for generation of functional mature beta cells from human pluripotent stem cell-derived endocrine progenitors according to embodiment 7, wherein concentration of Alk5iII is 10 µM.

12. The method for generation of functional mature beta cells from human pluripotent stem cell-derived endocrine progenitors according to embodiment 1, wherein concentration of Heparin is below 1 µg/ml.

13. The method for generation of functional mature beta cells from human pluripotent stem cell-derived endocrine progenitors according to embodiment 1, wherein concentration of Heparin is 1 µg/ml.

14. The method for generation of functional mature beta cells from human pluripotent stem cell-derived endocrine progenitors according to embodiment 1, wherein concentration of Heparin is in a range of 1-10 µg/ml.

15. The method for generation of functional mature beta cells from human pluripotent stem cell-derived endocrine progenitors according to embodiment 1, wherein concentration of Heparin is 10 µg/ml.

16. The method for generation of functional mature beta cells from human pluripotent stem cell-derived endocrine progenitors according to embodiment 1, wherein the concentration of Nicotinamide is below 1 mM.

17. The method for generation of functional mature beta cells from human pluripotent stem cell-derived endocrine progenitors according to embodiment 1, wherein the concentration of Nicotinamide is 1 mM.

18. The method for generation of functional mature beta cells from human pluripotent stem cell-derived endocrine progenitors according to embodiment 1, wherein the concentration of Nicotinamide is in a range of 1-10 mM.

19. The method for generation of functional mature beta cells from human pluripotent stem cell-derived endocrine progenitors according to embodiment 1, wherein the concentration of Nicotinamide is 10 mM.

20. The method for generation of functional mature beta cells from human pluripotent stem cell-derived endocrine progenitors according to embodiment 1, comprising the step of (1) culturing the stem cell-derived endocrine progenitor cells in a medium comprising DZNep, Alk5iII, Heparin and Nicotinamide.

21. The method for generation of functional mature beta cells from human pluripotent stem cell-derived endocrine progenitors according to embodiment 1, comprising the step of (1) culturing the stem cell-derived endocrine progenitor cells in a medium comprising 1 µM DZNep, 10 µM Alk5iII, 10 µg/ml Heparin and 10 mM Nicotinamide.

22. The method for generation of functional mature beta cells from human pluripotent stem cell-derived endocrine progenitors according to embodiment 1, comprising step (1) in combination with one or more additional agent.

23. The method for generation of functional mature beta cells from human pluripotent stem cell-derived endocrine progenitors according to embodiment 22, wherein the additional agent is selected from a group consisting of gamma-secretase inhibitor, cAMP-elevating agent, thyroid hormone signaling pathway activator and combinations thereof.

24. The method for generation of functional mature beta cells from human pluripotent stem cell-derived endocrine progenitors according to embodiment 23, wherein the additional agent is gamma-secretase inhibitor.

25. The method for generation of functional mature beta cells from human pluripotent stem cell-derived endocrine progenitors according to embodiment 24, wherein gamma-secretase inhibitor is N-[(3,5-Difluorophenyl)acetyl]-L-alanyl-2-phenyl]glycine-1,1-dimethylethyl ester (DAPT).

26. The method for generation of functional mature beta cells from human pluripotent stem cell-derived endocrine progenitors according to embodiment 25, wherein the concentration of DAPT is below 2.5 µM.

27. The method for generation of functional mature beta cells from human pluripotent stem cell-derived endocrine progenitors according to embodiment 25, wherein the concentration of DAPT is 2.5 µM.

28. The method for generation of functional mature beta cells from human pluripotent stem cell-derived endocrine progenitors according to embodiment 25, wherein the concentration of DAPT is in a range of 2.5-10 µM.

29. The method for generation of functional mature beta cells from human pluripotent stem cell-derived endocrine progenitors according to embodiment 25, wherein the concentration of DAPT is 5 µM.

30. The method for generation of functional mature beta cells from human pluripotent stem cell-derived endocrine progenitors according to embodiment 25, wherein the concentration of DAPT is 10 µM.

31. The method for generation of functional mature beta cells from human pluripotent stem cell-derived endocrine progenitors according to embodiment 23, wherein the additional agent is cAMP-elevating agent.

32. The method for generation of functional mature beta cells from human pluripotent stem cell-derived endocrine progenitors according to embodiment 31, wherein cAMP-elevating agent is Dibutyryl-cAMP (dbcAMP).

33. The method for generation of functional mature beta cells from human pluripotent stem cell-derived endocrine progenitors according to embodiment 32, wherein the concentration of dbcAMP is below 250 µM.

34. The method for generation of functional mature beta cells from human pluripotent stem cell-derived endocrine progenitors according to embodiment 32, wherein the concentration of dbcAMP is 250 µM.

35. The method for generation of functional mature beta cells from human pluripotent stem cell-derived endocrine progenitors according to embodiment 32, wherein the concentration of dbcAMP is in a range of 250-500 µM.

36. The method for generation of functional mature beta cells from human pluripotent stem cell-derived endocrine progenitors according to embodiment 32, wherein the concentration of dbcAMP is 500 µM.

37. The method for generation of functional mature beta cells from human pluripotent stem cell-derived endocrine progenitors according to embodiment 23, wherein the additional agent is thyroid hormone signaling pathway activator.

38. The method for generation of functional mature beta cells from human pluripotent stem cell-derived endocrine progenitors according to embodiment 37, wherein thyroid hormone signaling pathway activator is T3.

39. The method for generation of functional mature beta cells from human pluripotent stem cell-derived endocrine progenitors according to embodiment 38, wherein the concentration of T3 is below 1 µM.

40. The method for generation of functional mature beta cells from human pluripotent stem cell-derived endocrine progenitors according to embodiment 38, wherein the concentration of T3 is 1 µM.

41. The method for generation of functional mature beta cells from human pluripotent stem cell-derived endocrine progenitors according to embodiment 38, wherein the concentration of T3 is in a range of 1-10 µM.

42. The method for generation of functional mature beta cells from human pluripotent stem cell-derived endocrine progenitors according to embodiment 38, wherein the concentration of T3 is 10 µM.

43. The method for generation of functional mature beta cells from human pluripotent stem cell-derived endocrine progenitors according to embodiment 1, comprising the step of (1) culturing the stem cell-derived endocrine progenitor cells in a medium comprising DZNep, Alk5iII, Heparin and Nicotinamide in combination with DAPT.

44. The method for generation of functional mature beta cells from human pluripotent stem cell-derived endocrine progenitors according to embodiment 1, comprising step of (1) culturing the stem cell-derived endocrine progenitor cells in a medium comprising 1 µM DZNep, 10 µNA Alk5iII, 10 µg/ml Heparin and 10 mM Nicotinamide in combination with 2.5 µM DAPT.

45. The method for generation of functional mature beta cells from human pluripotent stem cell-derived endocrine progenitors according to embodiment 1, comprising step of (1) culturing the stem cell-derived endocrine progenitor cells in a medium comprising DZNep, Alk5iII, Heparin and Nicotinamide in combination with dbcAMP.

46. The method for generation of functional mature beta cells from human pluripotent stem cell-derived endocrine progenitors according to embodiment 1, comprising step (1) culturing the stem cell-derived endocrine progenitor cells in a medium comprising 1 µM DZNep, 10 µM Alk5iII, 10 µg/ml Heparin and 10 mM Nicotinamide in combination with 250 µM dbcAMP.

47. The method for generation of functional beta cells from human pluripotent stem cell-derived endocrine progenitors according to embodiment 23, wherein the additional agent gamma-secretase inhibitor is in combination with thyroid hormone signaling pathway activator.

48. The method for generation of functional mature beta cells from human pluripotent stem cell-derived endocrine progenitors according to embodiment 47, wherein the additional agent DAPT is in combination with T3.

49. The method for generation of functional mature beta cells from human pluripotent stem cell-derived endocrine progenitors according to embodiment 48, wherein the concentration of DAPT is 2.5 µM and concentration of T3 is 1 µM.

50. The method for generation of functional mature beta cells from human pluripotent stem cell-derived endocrine progenitors according to embodiment 23, wherein the additional agent gamma-secretase inhibitor is in combination with cAMP elevating agent.

51. The method for generation of functional mature beta cells from human pluripotent stem cell-derived endocrine progenitors according to embodiment 50, wherein the additional agent is DAPT in combination with dbcAMP.

52. The method for generation of functional mature beta cells from human pluripotent stem cell-derived endocrine progenitors according to embodiment 51, wherein the concentration of DAPT is 2.5 µM and concentration of dbcAMP is 250 µM.

53. The method for generation of functional mature beta cells from human pluripotent stem cell-derived endocrine progenitors according to embodiment 1, wherein the stem cell-derived endocrine progenitor cells are cultured in step (1) for 1-4 days.

54. The method for generation of functional mature beta cells from human pluripotent stem cell-derived endocrine progenitors according to embodiment 1, wherein the stem cell-derived endocrine progenitor cells are cultured in step (1) for 4 days.

55. The method for generation of functional mature beta cells from human pluripotent stem cell-derived endocrine progenitors according to embodiment 1, wherein the stem cell-derived endocrine progenitor cells are cultured in step (1) for 4-7 days.

56. The method for generation of functional mature beta cells from human pluripotent stem cell-derived endocrine progenitors according to any of one preceding embodiments, wherein 10-60% INS+ and NKX6.1+ double positive immature beta cells are obtained in step 1.

57. The method for generation of functional mature beta cells from human pluripotent stem cell-derived endocrine progenitors according to any one the preceding embodiments, wherein 20-50% INS+ and NKX6.1+ double positive immature beta cells are obtained in step (1).

58. The method for generation of functional mature beta cells from human pluripotent stem cell-derived endocrine progenitors according to any of one preceding embodiments, wherein 25-45% INS+ and NKX6.1+ double positive immature beta cells are obtained in step 1.

59. The method for generation of functional mature beta cells from human pluripotent stem cell-derived endocrine progenitors according to any of one preceding embodiments, wherein 30-40% INS+ and NKX6.1+ double positive immature beta cells are obtained in step 1.

60. The method for generation of functional mature beta cells from human pluripotent stem cell-derived endocrine progenitors according to embodiment 1, comprising culturing the beta cells obtained in step (1) with 12% KOSR and GABA, in combination with one or more additional agent to obtain functional mature beta cells.

61. The method for generation of functional mature beta cells from human pluripotent stem cell-derived endocrine progenitors according to embodiment 60, wherein the concentration of GABA is 50 µM.

62. The method for generation of functional mature beta cells from human pluripotent stem cell-derived endocrine progenitors according to embodiment 60, wherein the concentration of GABA is in a range of 50-250 µM.

63. The method for generation of functional mature beta cells from human pluripotent stem cell-derived endocrine progenitors according to embodiment 60, wherein the concentration of GABA is 250 µM.

61. The method for generation of functional mature beta cells from human pluripotent stem cell-derived endocrine progenitors according to embodiment 60, wherein additional agent is TGF-beta signaling pathway inhibitor.

62. The method for generation of functional mature beta cells from human pluripotent stem cell-derived endocrine progenitors according to embodiment 61, wherein TGF-beta signaling pathway inhibitor is Alk5iII.

63. The method for generation of functional mature beta cells from human pluripotent stem cell-derived endocrine progenitors according to embodiment 62, wherein the concentration of Alk5iII is below 1 µM.

64. The method for generation of functional mature beta cells from human pluripotent stem cell-derived endocrine progenitors according to embodiment 62, wherein the concentration of Alk5iII is 1 µM.

65. The method for generation of functional mature beta cells from human pluripotent stem cell-derived endocrine progenitors according to embodiment 62, wherein the concentration of Alk5iII is in a range of 1-10 µM.

66. The method for generation of functional mature beta cells from human pluripotent stem cell-derived endocrine progenitors according to embodiment 62, wherein the concentration of Alk5iII is 10 µM.

67. The method for generation of functional mature beta cells from human pluripotent stem cell-derived endocrine progenitors according to embodiment 60, wherein additional agent is thyroid hormone signaling pathway activator.

68. The method for generation of functional mature beta cells from human pluripotent stem cell-derived endocrine progenitors according to embodiment 67, wherein thyroid hormone signaling pathway activator is T3.

69. The method for generation of functional mature beta cells from human pluripotent stem cell-derived endocrine progenitors according to embodiment 68, wherein the concentration of T3 is below 1 µM.

70. The method for generation of functional mature beta cells from human pluripotent stem cell-derived endocrine progenitors according to embodiment 68, wherein the concentration of T3 is 1 µM.

71. The method for generation of functional mature beta cells from human pluripotent stem cell-derived endocrine progenitors according to embodiment 68, wherein the concentration of T3 is in a range of 1-10 µM.

72. The method for generation of functional mature beta cells from human pluripotent stem cell-derived endocrine progenitors according to embodiment 68, wherein the concentration of T3 is 10 µM.

73. The method for generation of functional mature beta cells from human pluripotent stem cell-derived endocrine progenitors according to embodiment 60, wherein additional agent is histone methyltransferase EZH2 inhibitor.

74. The method for generation of functional mature beta cells from human pluripotent stem cell-derived endocrine progenitors according to embodiment 73, wherein histone methyltransferase EZH2 inhibitor is DZNep.

75. The method for generation of functional mature beta cells from human pluripotent stem cell-derived endocrine progenitors according to embodiment 74, wherein the concentration of DZNep is below 1 µM.

76. The method for generation of functional mature beta cells from human pluripotent stem cell-derived endocrine progenitors according to embodiment 74, wherein the concentration of DZNep is in a range of 1-10 µM.

77. The method for generation of functional mature beta cells from human pluripotent stem cell-derived endocrine progenitors according to embodiment 74, wherein the concentration of DZNep is 10 µM.

78. The method for generation of functional mature beta cells from human pluripotent stem cell-derived endocrine progenitors according to embodiment 60, wherein additional agent TGF-beta signaling pathway inhibitor is in combination with thyroid hormone signaling pathway activator and histone methyltransferase EZH2 inhibitor is DZNep.

79. The method for generation of functional mature beta cells from human pluripotent stem cell-derived endocrine progenitors according to embodiment 78, wherein additional agent Alk5iII in combination with T3 and DZNep.

80. The method for generation of functional mature beta cells from human pluripotent stem cell-derived endocrine progenitors according to embodiment 79, wherein additional agent 10 µM Alk5iII in combination with 1 µM T3 and 1 µM DZNep.

81. The method for generation of functional mature beta cells from human pluripotent stem cell-derived endocrine progenitors according to embodiment 60, wherein additional agent TGF-beta signaling pathway inhibitor is in combination with thyroid hormone signaling pathway activator.

82. The method for generation of functional mature beta cells from human pluripotent stem cell-derived endocrine progenitors according to embodiment 81, wherein additional agent Alk5iII in combination with T3.

83. The method for generation of functional mature beta cells from human pluripotent stem cell-derived endocrine progenitors according to embodiment 82, wherein 10 µM Alk5iII is in combination with 1 µM T3.

84. The method for generation of functional mature beta cells from human pluripotent stem cell-derived endocrine progenitors according to embodiment 60, wherein additional agent TGF-beta signaling pathway inhibitor is in combination with histone methyltransferase EZH2 inhibitor is DZNep.

85. The method for generation of functional mature beta cells from human pluripotent stem cell-derived endocrine progenitors according to embodiment 84, wherein additional agent Alk5iII in combination with DZNEP.

86. The method for generation of functional mature beta cells from human pluripotent stem cell-derived endocrine progenitors according to embodiment 85, wherein 10 µM Alk5iII is in combination with 1 µM DZNEP.

87. The method for generation of functional mature beta cells from human pluripotent stem cell-derived endocrine progenitors according to any of one preceding embodiments 60-86, wherein INS+ and NKX6.1+ double positive immature beta cells obtained in step (1) are cultured in step (2) for 3-7 days.

88. The method for generation of functional mature beta cells from human pluripotent stem cell-derived endocrine progenitors according to any of one preceding embodiments 60-86, wherein INS+ and NKX6.1+ double positive immature beta cells obtained in step (1) are cultured in step (2) for 7-11 days.

89. The method for generation of functional mature beta cells from human pluripotent stem cell-derived endocrine progenitors according to any of one embodiments 60-86, wherein 10-60% functional mature beta cells are obtained in step 2.

90. The method for generation of functional mature beta cells from human pluripotent stem cell-derived endocrine progenitors according to any of one embodiments 60-86, wherein 20-50% functional mature beta cells are obtained in step 2.

91. The method for generation of functional mature beta cells from human pluripotent stem cell-derived endocrine progenitors according to any of one embodiments 60-86, wherein 25-45% functional mature beta cells are obtained in step 2.

92. The method for generation of functional mature beta cells from human pluripotent stem cell-derived endocrine progenitors according to any of one embodiments 60-86, wherein 30-40% functional mature beta cells are obtained in step 2.

93. Functional mature beta cells obtainable by method according to any one of embodiments 1-92.

94. Functional mature beta cells obtained in embodiment 93 express MAFA, IAPP and G6PC2.

In one embodiment, the cells obtainable by the method according to the invention are insulin producing cells, optionally together with cells differentiated towards glucagon, somatostatin, pancreatic polypeptide, and/or ghrelin producing cells. As used herein, "insulin producing cells" refers to cells that produce and store or secrete detectable amounts of insulin. "Insulin producing cells" can be individual cells or collections of cells.

In another embodiment, the cell population comprising pancreatic cells is obtained from a somatic cell population. In some aspects the somatic cell population has been induced to de-differentiate into an embryonic-like stem (ES, e.g., a pluripotent) cell. Such de-differentiated cells are also termed induced pluripotent stem cells (iPSC).

In another embodiment, the cell population comprising pancreatic cells is obtained from embryonic stem (ES, e.g., pluripotent) cells. In some aspects the cell population comprising pancreatic cells is pluripotent cells such as ES like-cells.

In another embodiment, the cell population comprising pancreatic cells is embryonic differentiated stem (ES or pluripotent) cells. Differentiation takes place in embryoid bodies and/or in monolayer cell cultures or a combination thereof.

In another embodiment, the cell population is a population of stem cells. In some aspects the cell population is a population of stem cells differentiated to the pancreatic endocrine lineage.

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multi-potent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multi-potent stem cells; and (5) unipotent, meaning able to give rise to a single cell lineage (e.g., spermatogenic stem cells).

As used herein "differentiate" or "differentiation" refers to a process where cells progress from an undifferentiated state to a differentiated state, from an immature state to a less immature state or from an immature state to a mature state. For example, early undifferentiated embryonic pancreatic cells are able to proliferate and express characteristics markers, like PDX1, NKX6.1, and PTF1a. Mature or differentiated pancreatic cells do not proliferate and do secrete high levels of pancreatic endocrine hormones or digestive enzymes. E.g., fully differentiated beta cells secrete insulin at high levels in response to glucose. Changes in cell interaction and maturation occur as cells lose markers of undifferentiated cells or gain markers of differentiated cells. Loss or gain of a single marker can indicate that a cell has "matured or fully differentiated." The term "differentiation factor" refers to a compound added to pancreatic cells to enhance their differentiation to mature endocrine cells also containing insulin producing beta cells. Exemplary differentiation factors include hepatocyte growth factor, keratinocyte growth factor, exendin-4, basic fibroblast growth factor, insulin-like growth factor-1, nerve growth factor, epidermal growth factor platelet-derived growth factor, and glucagon-like peptide 1. In some aspects differentiation of the cells comprises culturing the cells in a medium comprising one or more differentiation factors.

As used herein, "human pluripotent stem cells" (hPSC) refers to cells that may be derived from any source and that are capable, under appropriate conditions, of producing human progeny of different cell types that are derivatives of all of the 3 germinal layers (endoderm, mesoderm, and ectoderm). hPSC may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in 30 literature often denoted as human embryonic stem (hES) cells, (see, e.g., Thomson et al. (1998), Heins et al. (2004), as well as induced pluripotent stem cells (see, e.g. Yu et al. (2007); Takahashi et al. (2007)). The various methods and other embodiments described herein may require or utilise hPSC from a variety of sources. For example, hPSC suitable for use may be obtained from developing embryos. Additionally or alternatively, suitable hPSC may be obtained from established cell lines and/or human induced pluripotent stem (hiPS) cells.

As used herein "hiPSC" refers to human induced pluripotent stem cells.

As used herein, the term "blastocyst-derived stem cell" is denoted BS cell, and the human form is termed "hBS cells". In literature the cells are often referred to as embryonic stem cells, and more specifically human embryonic stem cells (hESC). The pluripotent stem cells used in the present invention can thus be embryonic stem cells prepared from blastocysts, as described in e.g. WO 03/055992 and WO 2007/042225, or be commercially available hBS cells or cell lines. However, it is further envisaged that any human pluripotent stem cell can be used in the present invention, including differentiated adult cells which are reprogrammed to pluripotent cells by e.g. the treating adult cells with certain transcription factors, such as OCT4, SOX2, NANOG, and LIN28 as disclosed in Yu, et al. (2007); Takahashi et al. (2007) and Yu et al. (2009).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

LIST OF ABBREVIATIONS

AA: Activin A
BC: Beta cells
bFGF: basic fibroblast growth factor (FGF2)
D'Am: D'Amour protocol (Kroon et al., 2008)
DAPT: N-[(3,5-Difluorophenyl)acetyl]-L-alanyl-2-phenyl] glycine-1,1-dimethylethyl ester
DE: definitive endoderm
DZNep: 3-Deazaneplanocin A
EP: Endocrine Progenitor
FC: Flow cytometry
GABA: gamma-Aminobutyric acid
GSIS: glucose stimulated insulin secretion
hESC: human embryonic stem cells
hIPSC: human induced pluripotent cells
hPSC: human pluripotent stem cells
KOSR: knockout serum replacement
PE: Pancreatic Endoderm
RNA: ribonucleic acid
PCR: polymerase chain reaction
PS: primitive streak

EXAMPLES

In general, the process of differentiating hPSCs to functional mature beta cells goes through various stages. An exemplary method for generating functional beta cells from hPSCs in vitro is outlined in FIG. 1.

Example 1: Preparation of Endocrine Progenitor Cells hESCs (SA121) were cultured in DEF media (Cellectis) supplemented with 30 ng/mLbFGF (Peprotech #100-18B) and 10 ng/mL noggin (Peprotech #120-10C).

For adherent cultures, the hESCs were differentiated into DE in T75 flasks using a Chir99021 and ActivinA based protocol in WO2012/175633. DE was trypsinized using Tryple Select (Invitrogen #12563-029) and reseeded as single cells in RPMI1640 supplemented with 100 ng/ml ActivinA (Peprotech #120-14E), 2% B27 (Invitrogen #17504-044) and 0.1% PEST (Gibco #15140) in T75 flasks at 200 K/cm2. DE cells were allowed to attach and differentiated into PE using a LDN, AM508 based protocol in WO 2014/033322 followed by a four day EP protocol in WO2015/028614.

To produce large numbers of beta cells, a scalable suspension-based culture system was utilized by differentiating clusters of hESCs into DE in shaker flasks in Multitron Standard incubators (Infors) as suspension cultures (1 million/ml) at 70 RPM using a Chir99021 and ActivinA based protocol in WO2012/175633 without requirement of a reseeding step. DE cells were further differentiated into PE using a LDN, AM508 based protocol in WO 2014/033322 with the following slight modification: LDN is not added at PE day 4-10. Generation of PE was followed by a four day EP protocol WO2015/028614.

Example 2: Screening for Factors that Induce INS+/NKX6.1+Co-Expression During BC Step 1

As a first step towards generating fully functional mature beta cells, we screened for factors to generate maximal numbers of immature INS+/NKX6.1+ cells (BC step 1 screen). BC step 1 screen was initiated at the EP stage using library of kinase inhibitors, epigenetic regulators, redox and bioactive lipids supplemented with some literature based compounds (in total 650 compounds of interests) added on top of RPMI1640+2% B27+10 mM Nicotinamide.

Figure 2:
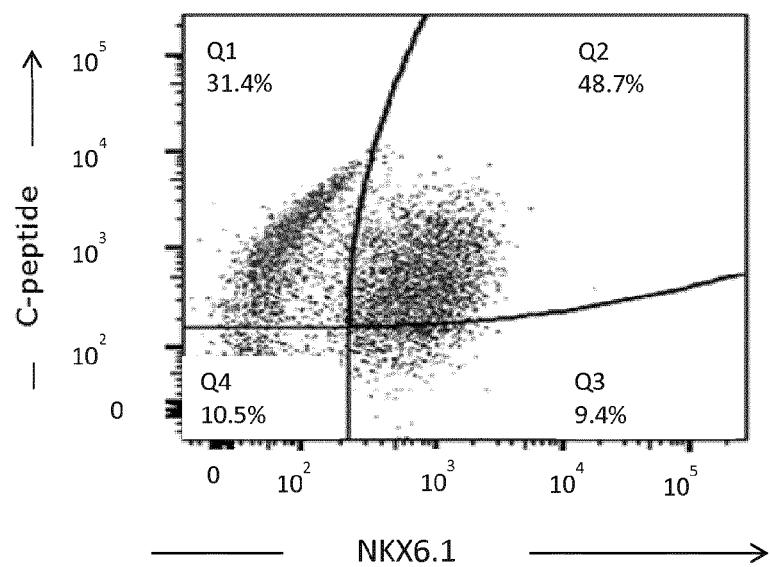
FIG. 2 shows effect of compounds on INS+/NKX6.1+/GCG− expression at day 4 of BC step 1 measured by Flow cytometry (FC).
Figure 2:
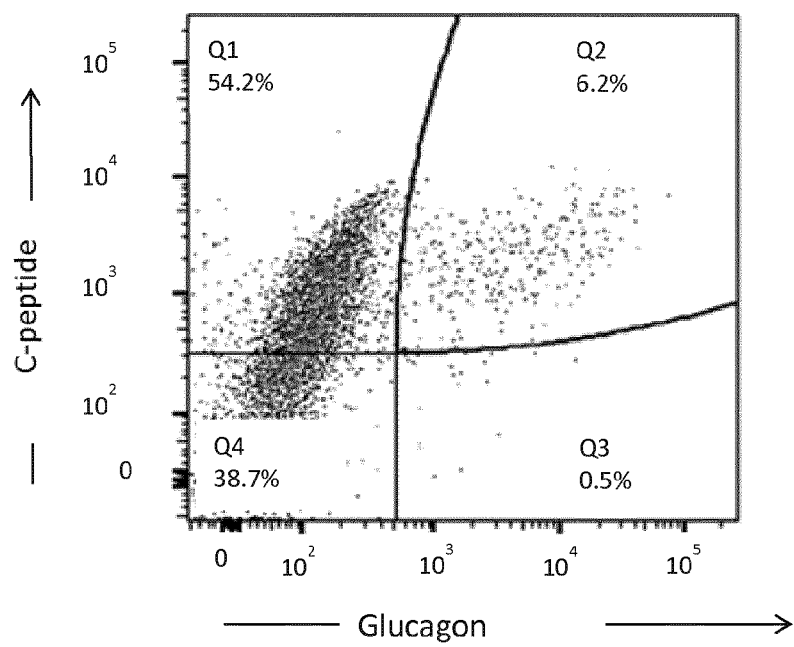

Compounds were screened for their ability to induce INS+, NKX6.1+ double positive immature BCs and few GCG positive cells within a 7 days period. Media change was performed daily. Cells were fixed at day 4 and day 7 of BC step 1 and analysed for INS NKX6.1 and GCG expression using flow cytometry (see Table 1 and FIG. 2). Briefly, cells were dispersed into single-cell suspension by incubation with TrypLE Express at 37° C. for 10 min. Cells were resuspended in 4% paraformaldehyde, washed in PBS followed by incubation with primary antibodies overnight and then secondary antibodies for 1 hour. The differentiated hPSCs co-expressed C-peptide+/NKX6-1+ with few cells expressing the α-cell hormone glucagon (FIG. 2). When quantified by flow cytometry, 48% of the cells co-expressed C-peptide+/NKX6-1, more than previously reported with stem cell-derived beta cells (reference Melton, Kieffer).

TABLE 1

FC analysis of BC step 1 method at BC day 7

|  | #1 |
|---|---|
| INS+/NKX6.1+ | 20.8% |
| INS+/NKX6.1− | 19.8% |
| INS−/NKX6+ | 16.4% |
| INS/GCG | 12.3% |
| INS+/GCG− | 25.6% |
| INS−/GCG+ | 2% |

1: DZNEP 1 uM + Alk5i 10 uM + 10 ug/ml Heparin

Figure 3:
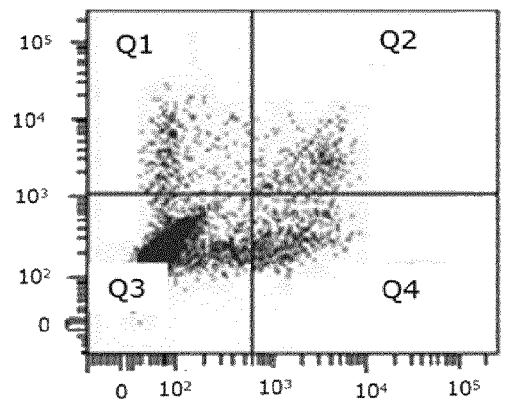
FIG. 3 shows additive effect when combining hits during BC step 1 on INS+/NKX6.1+ cell number.
Figure 3:
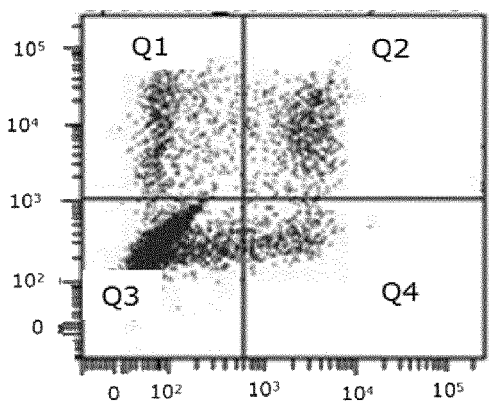
Figure 3:
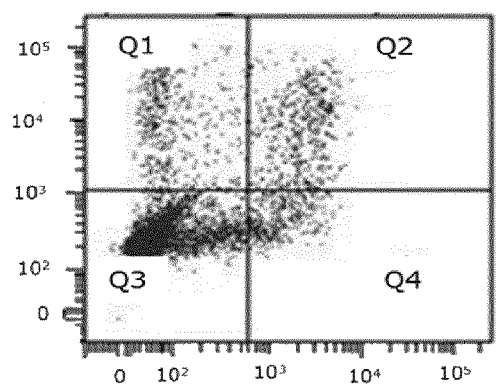
Figure 4:
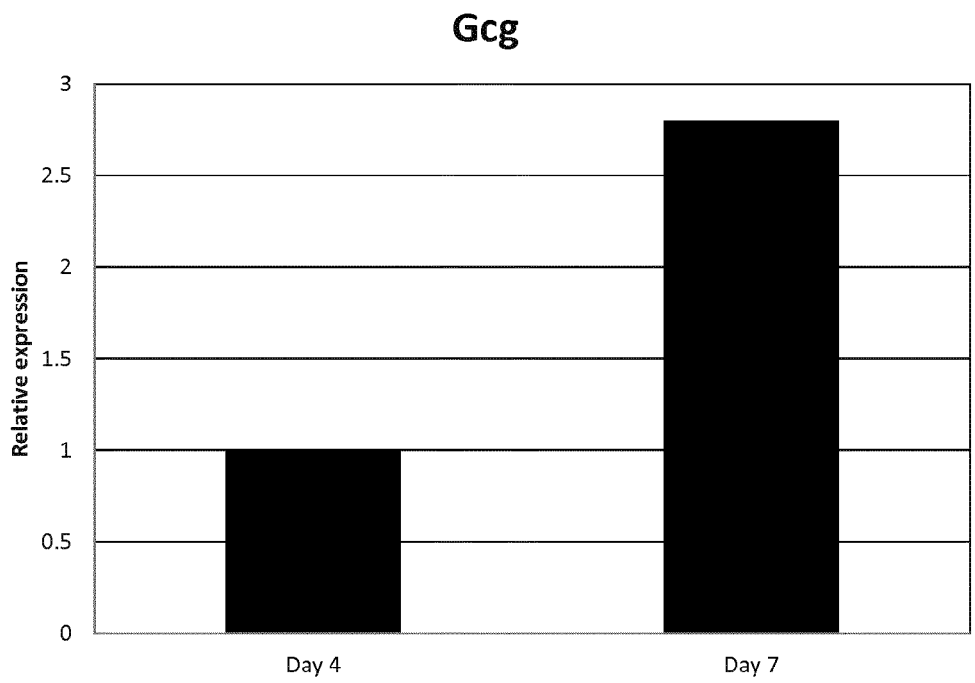
FIG. 4 shows timing studies of BC step 1 method.
Figure 4:
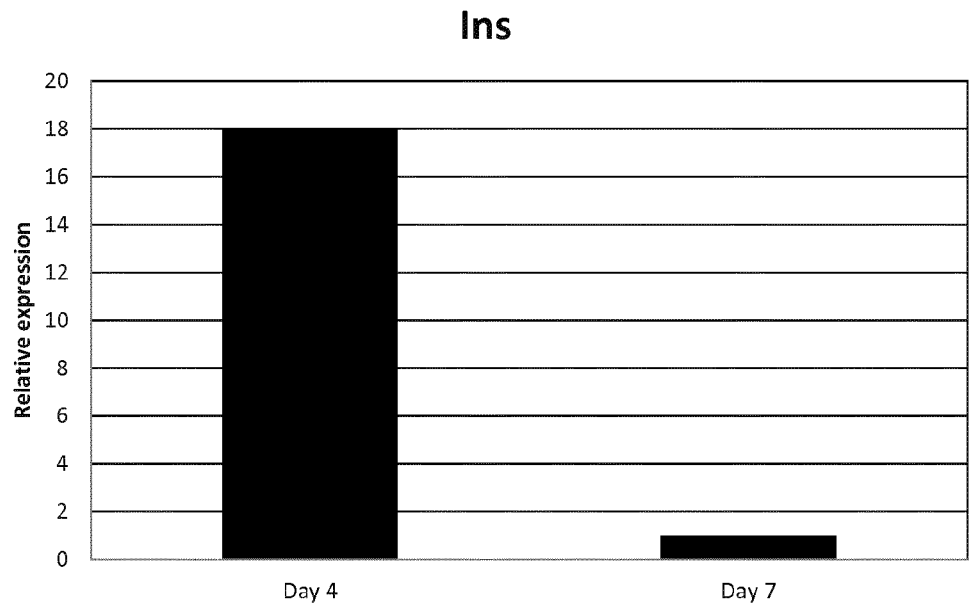

Hits identified in a primary screen were then combined individually and added on top of the BC step 1 medium (see Table 2 and FIG. 3). Timing of studies revealed that BC step 1 has an optimal length of 4-7 days based on mRNA expression of Ins and Gcg (see FIG. 4).

TABLE 2 shows hit compounds in BC step 1 medium

| Compound name | Target | Structure | Concentration |
|---|---|---|---|
| DAPT | Notch | [structure] | 2.5 μM |
| ALK5iII | TGF-β RI Kinase | [structure] | 1 μM, 10 μM |
| DZNEP | PRC complex? | [structure] •HCl | 1 μM, 10 μM |

TABLE 2-continued shows hit compounds in BC step 1 medium

| Compound name | Target | Structure | Concentration |
|---|---|---|---|
| Heparin | | | 10 µg/ml |
| dbcAMP | Increased cAMP levels | 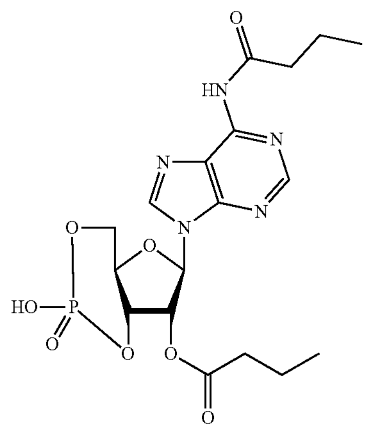 | 250 µM, 500 µM |
| Nicotinamide | | 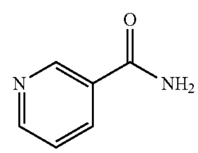 | 10 mM |
| T3 | Thyroid receptor | 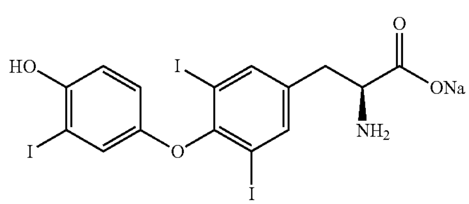 | 1 µM, 10 µM |

Example 3: Generation of Glucose Sensing Insulin Secreting Beta Cells from BC Step 1

The key functional feature of a fully functional mature beta cell is its ability to perform glucose stimulated insulin secretion (GSIS). We screened for factors in BC step 2 that could induce functional beta cells from the immature INS+/NKX6.1+ cells from BC step 1.

BC step 2 screen was performed in suspension cultures. For adherent cultures, cells in T75 flasks were trypsinized at the end of BC step 1 using Tryple Select and transferring cells into low attachment 9 cm petri dishes in suspension with RPMI1640 medium (Gibco #61870) containing 12% KOSR (ThermoFisher #10828028) and 0.1% PEST, Gibco #15140.

Figure 5:
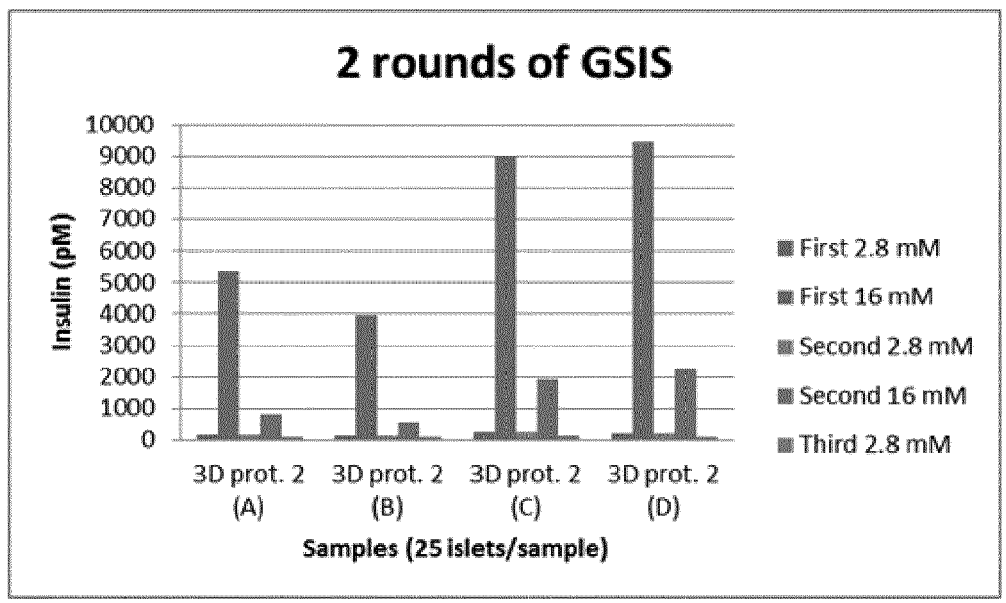
FIG. 5 shows effect of compounds added for 7 days during BC step 2 method on static GSIS.

Effects of selected compounds were then tested for a 7 day period for induction of glucose-responsive cells in a static GSIS setup (see FIG. 5). Briefly, cell clusters were sampled and incubated overnight in 2.8 mM glucose media to remove residual insulin. Clusters were washed two times in Krebs buffer, incubated in 2.8 mM Krebs buffer for 30 min, and supernatant collected. Then clusters were incubated in 16 mM glucose Krebs buffer for 30 min, and supernatant collected. This sequence was repeated. Finally, clusters were incubated in Krebs buffer containing 2.8 mM glucose for 30 min and then supernatant collected. Supernatant samples containing secreted insulin were processed using Human Insulin ELISA (Mercodia).

Hits identified in a primary screen were then combined individually and added on top of the 12% KOSR medium to generate the optimal 7-day BC step 2 protocol (see Table 3).

TABLE 3 shows hit compounds in BC step 2 medium

| Compound name | Target | Structure | Concentration |
|---|---|---|---|
| T3 | Thyroid receptors | 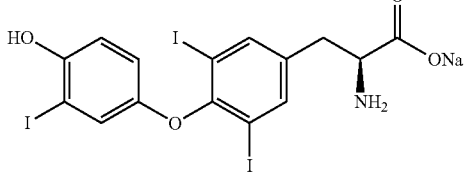 | 1 µM, 10 µM |
| ALK5iII | TGF-β RI Kinase | 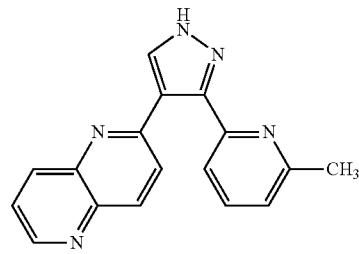 [SMILES: Cc1cccc(-c2n[nH]cc2-c2ccc3ncccc3n2)n1] | 1 µM, 10 µM |
| dbcAMP | cAMP | 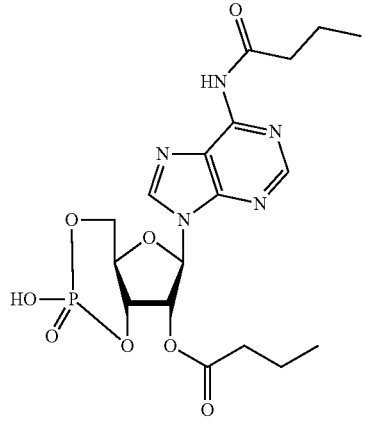 | 250 µM |
| GABA | GABA receptors | 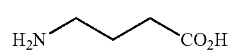 | 50 µM |
| KOSR | | | 12% |

Example 4: Perfusion Assay to Assay Dynamic Human Insulin Secretion In Vitro Mature beta cells are functionally defined by their rapid response to elevated glucose. Secretion of human insulin by beta cells at the end of BC step 2 was measured as repeated responses to 20 mM glucose±1 µM exendin-4 or ±the anti-diabetic sulfonylurea compound Tolbutamide within a perfusion system.

Briefly, groups of 300 hand-picked, clusters of hESC- or hiPSC-derived cell clusters were suspended with beads (Bio-Rad #150-4124) in plastic chambers of Biorep PERFUSION SYSTEM (Biorep #PERI-4.2). Under temperature- and CO2-controlled conditions, the cells were perfused at 0.5 ml min-1 with a Krebs buffer. Prior to sample collection, cells were equilibrated under basal (2 mM glucose) conditions for 1 h. During perfusion cells were exposed to repeated challenges with 20 mM glucose±1 µM exendin-4 or ±100 µM Tolbutamide. At the end of perfusion, cells were exposed to cAMP-elevating agents on top of 20 mM glucose. Insulin secretion was measured by human insulin ELISA (Mercodia).

Figure 6A:
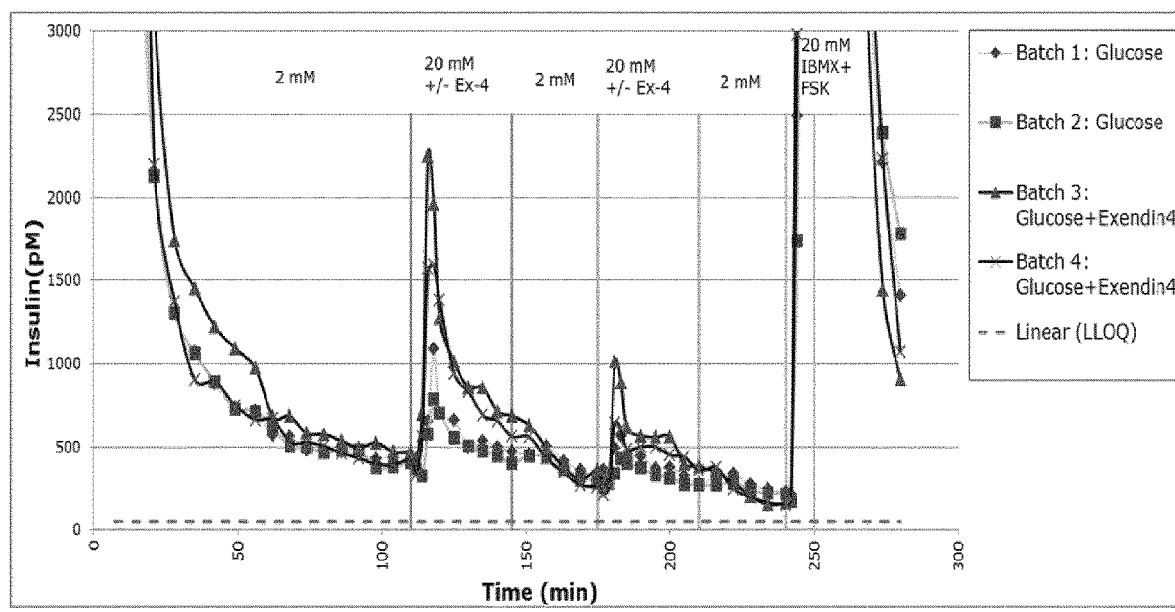
FIG. 6A shows presence of glucose responsive insulin secreting cells at day 3 of BC step 2.
Figure 6B:
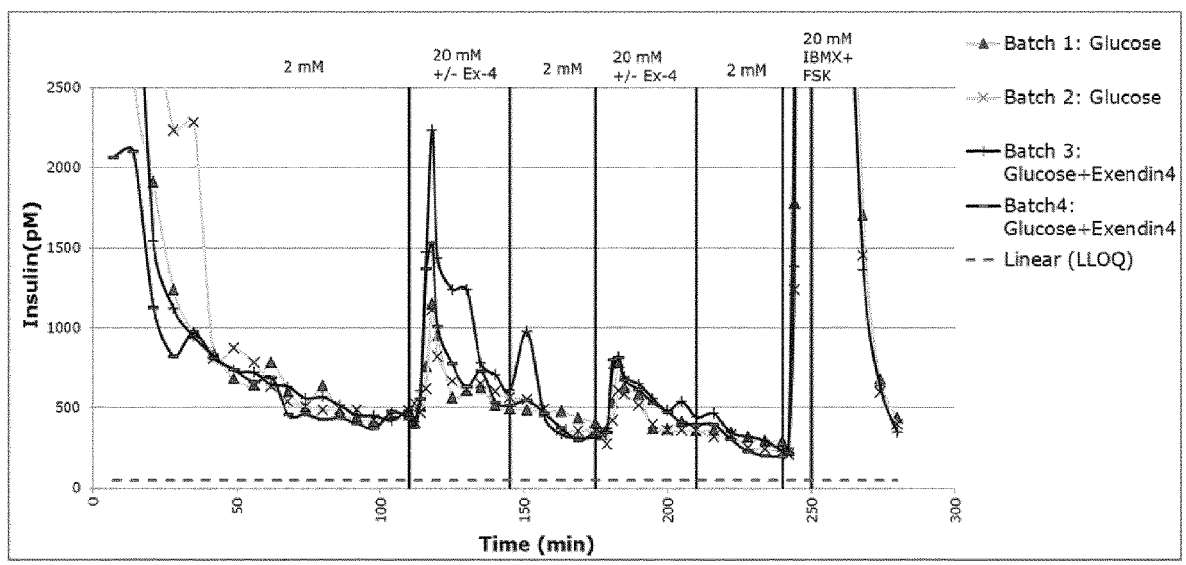
FIG. 6B shows presence of glucose responsive insulin secreting cells at day 7 of BC step 2.

By perfusion analysis, our stem cell-derived beta cells exhibited rapid and robust release of insulin with a $1^{st}$ and $2^{nd}$ phase of insulin secretion that was highly synchronized with changes in glucose concentrations (see FIG. 6). The GLP-1 analog exendin-4 increased the level of insulin secretion in the hPSC-derived beta cells. Importantly, presence of glucose responsive insulin secreting cells was observed for at least 4 days in vitro as measured at day 3 (FIG. 6A) and day 7 (FIG. 6B) of BC step 2.

Figure 7:
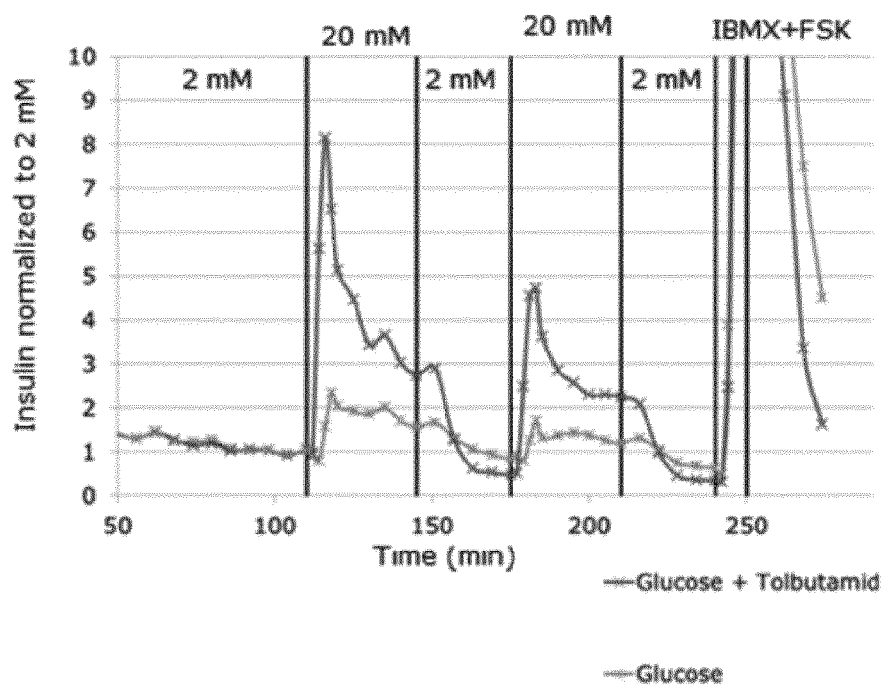
FIG. 7 shows functionality of hESC-derived beta cells demonstrated by dose dependent glucose and sulfonylurea mediated insulin release in a dynamic fashion
Figure 8:
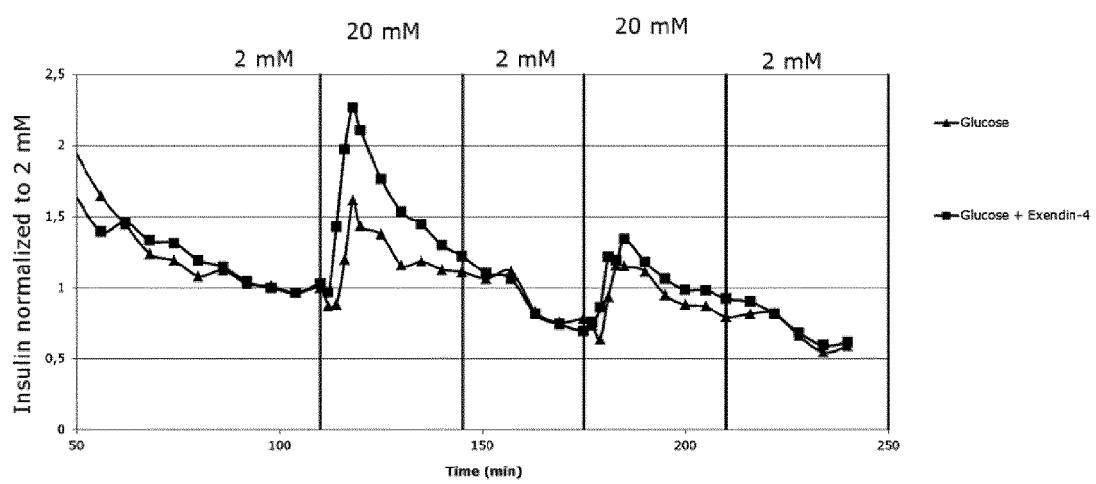
FIG. 8 shows robust protocol induced functional beta cells from independent pluripotent cell lines.
Figure 8:
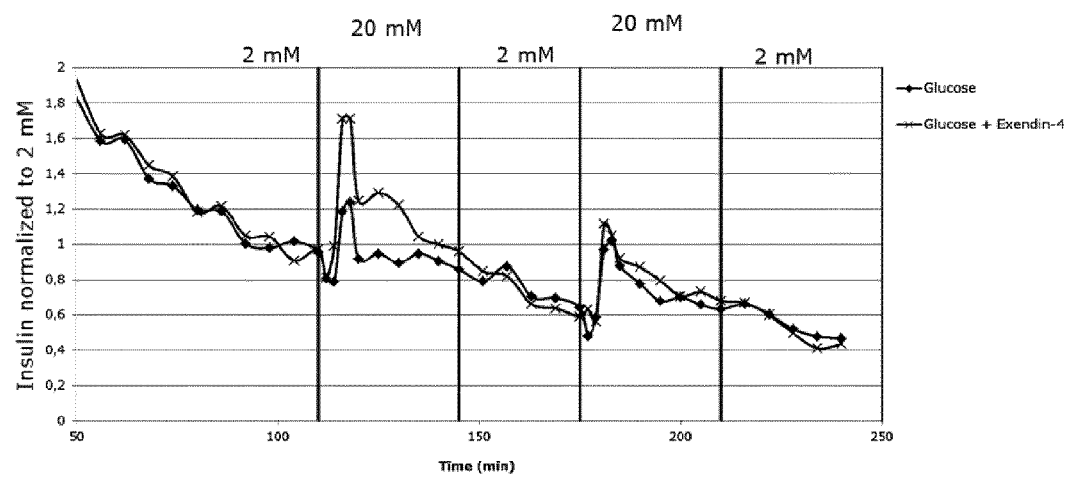

Another example of perifusion analysis of our stem cell-derived beta cells at day 7 of BC step 2 demonstrated a significant additive effect of the sulfonylurea tolbutamide on insulin secretion (FIG. 7). Robustness of the protocol is demonstrated by induction of functional beta cells from independent pluripotent cell lines (see FIG. 8). These data demonstrate collectively the superiority of the protocol for generating stem cell-derived beta cells that display glucose-stimulated insulin release dynamics measured by perifusion as compared to previous reports (Rezania, 2014; Paglucia, 2014 and review Johnson-J, 2016 Diabetologia).

Figure 9:
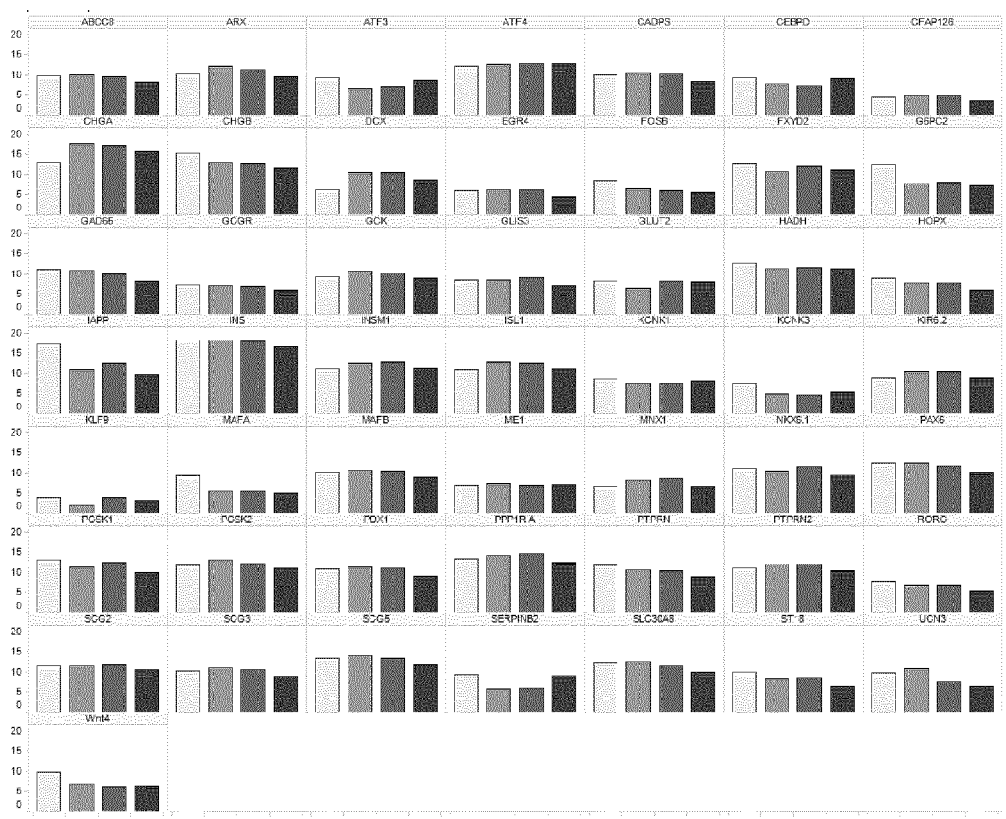
FIG. 9 Beta cell specific genes expressed in stem cell-derived beta cells at day 9 of BC step 2

Example 5 Gene Expression Analysis Showed High Level of Similarities of Stem Cell-Derived Beta Cells to Human Islet Material Differentiated cell clusters at BC day 7 of step 2 or human islets were collected and RNA was purified using the RNeasy kit from Qiagen (Cat No. ID: 74134). The quality was assessed using the RNA 6000 Nano Kit and the 2100 Bianalyser instrument (Agilent). 100 ng RNA was subjected to an nCounter assay according to instructions from Nanostring Technology. FIG. 9 shows the expression profile of beta cell associated genes from human islets and beta cells generated from hiPSC and two different hESC lines. The gene expression analysis showed that the stem cell-derived beta cells had close molecular resemblance to human islets.

Figure 10:
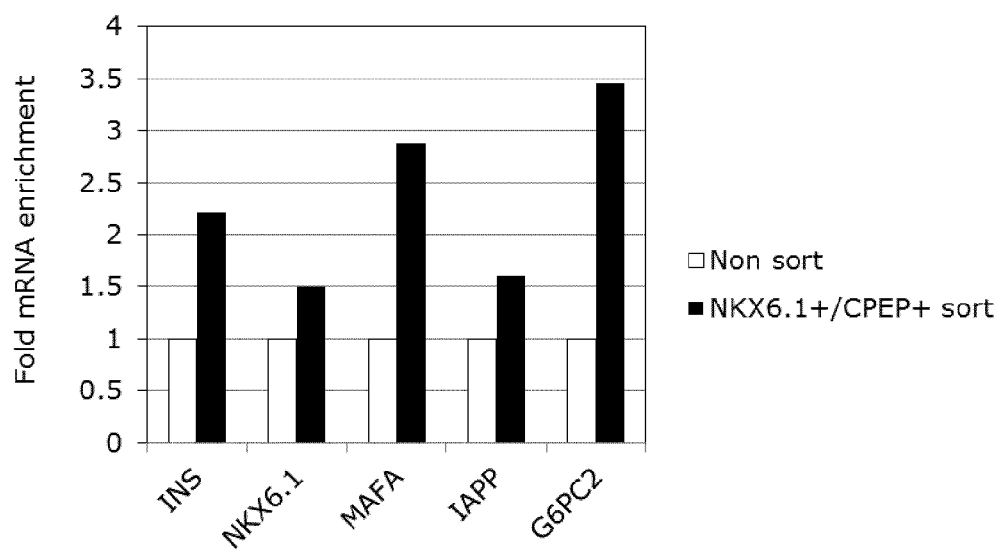
FIG. 10 shows enrichment of beta cell markers by sorting for INS+/NKX6.+ cells

Additional gene expression analysis of the specific stem cell-derived INS+/NKX6.1+ cells were performed by FACS cell sorting. Prior to sorting on the BD FACSARIA Fusion™ instrument, cell clusters were dissociated and stained for the separation of live and dead cells using a near IR dye (Thermo Scientific). After fixation and permeabilisation the cells were stained using the intracellular markers NKX6.1 and C-peptide. RNA was purified using the RNeasy FFPE Kit (QIAGEN) and quality was assessed using the RNA 6000 Nano Kit and the 2100 Bianalyser instrument (Agilent). FIG. 10 shows enrichment of key beta cell maturity genes after cell sorting for NKX6.1/CPEP double positive cells. Nanostring data was normalized to the unsorted cell population.

Example 6 Stem Cell-Derived Beta Cells from Step 2 Function after Transplantation To evaluate functionality in vivo, stem cell-derived beta cells from day 3-10 of BC step 2 were transplanted into a streptozotocin-induced mouse model of diabetes. In short, diabetes is induced in immunocompromised scid-beige mice (Taconic) using Multiple Low Dose (5×70 mg/kg) Streptozotocin (STZ), the mice are fasted 4 h prior to STZ dosing. The mice are monitored over the following weeks with respect to blood glucose, body weight and HbA1c. Diabetes is considered when blood glucose is consistently above 16 mM.

In full anaesthesia and analgesia the diabetic mice are transplanted with $5 \times 10^6$ human embryonic stem cell derived beta cells (unsorted population) under the kidney capsule. The kidney is exposed trough a small incision through skin and muscle of the left back side of the animal, a pouch between the parenchyma of the kidney and the capsule is created were the cell clusters are injected. The abdominal wall and the skin is closed and the mouse is allowed to recover.

Figure 11:
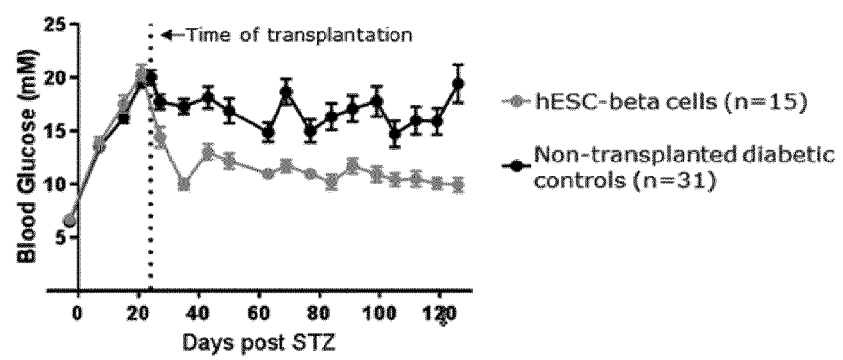
FIG. 11 shows diabetic mice transplanted with stem cell-derived beta cells show rapid lowering of blood glucose and reversal of diabetes
Figure 12:
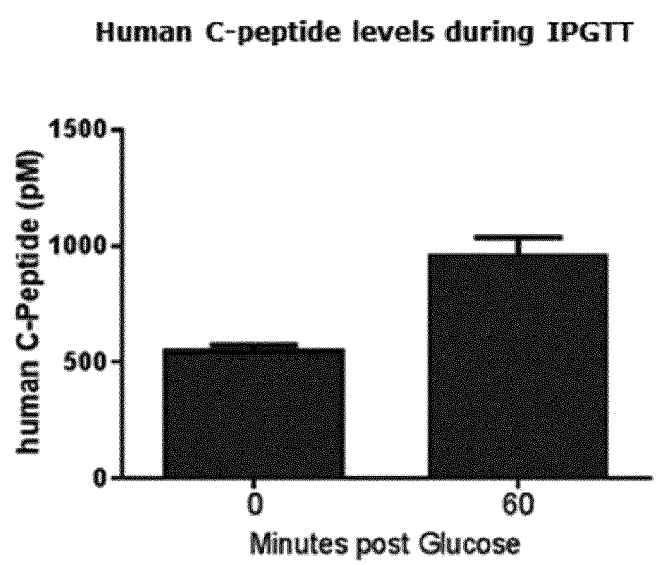
FIG. 12 shows intraperitoneal glucose tolerance test (IP-GTT) of transplanted cells
Figure 13:
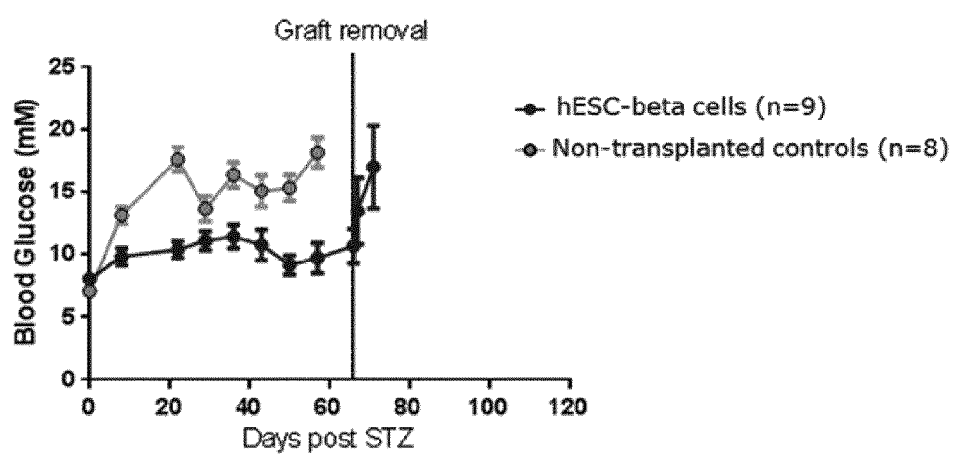
FIG. 13 shows stem cell derived beta cells protect against hyperglycemia post-streptozotocin treatment
Figure 14:
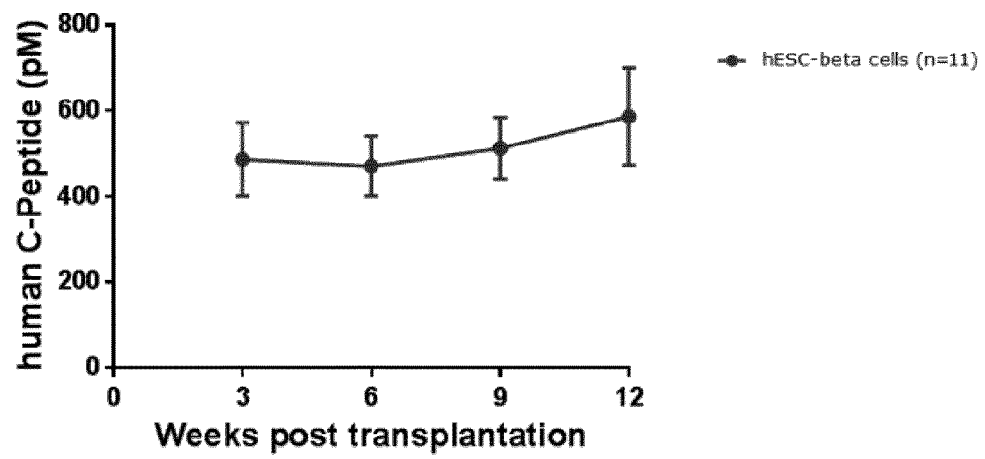
FIG. 14 shows high levels of circulating human C-peptide in transplanted mice

The function of the cells is monitored over the coming weeks with respect to blood glucose, body weight, HbA1c and human c-peptide/insulin secretion. Our stem cell-derived beta cells resulted in rapid reversal of diabetes within the first two weeks after transplantation (FIG. 11), more rapidly than previous reports (Rezania, 2014). Importantly, all mice with less than 85% of BW received daily injections with insulin, i.e. non-transplanted diabetic control group. In vivo challenge of transplanted cells with glucose demonstrated in vivo functionality of our stem cell-derived beta cells with better glucose clearance than control mice and increased level of circulating human c-peptide within 60 min of glucose injection (FIG. 12). In another diabetes model, 5 million differentiated cells were transplanted to the kidney capsule of non-diabetic SCID/Beige mice. These mice were then treated with streptozotocin 8 weeks after transplantation. FIG. 13 demonstrates that the pre-transplanted mice were protected from hyperglycemia post-streptozotocin administration versus non-transplanted control mice, whereas removal of the graft resulted in rapid hyperglycemia in the mice (see FIG. 13). High levels of circulating human c-peptide was measured in all transplanted mice from the first data point and until end of study (see FIG. 14).

The invention claimed is:

1. A method for generating functional mature beta cells from endocrine progenitor cells, comprising the steps of (1) culturing the endocrine progenitor cells in a basal medium comprising a histone methyltransferase EZH2 inhibitor, a TGF-beta signaling pathway inhibitor, Heparin, and Nicotinamide, to obtain INS+ and NKX6.1+ double positive immature beta cells and (2) culturing the immature beta cells obtained in step (1) with 12% KOSR and GABA, to obtain the functional mature beta cells; wherein the endocrine progenitor cells are differentiated from pancreatic endoderm cells.

2. The method according to claim 1, wherein the histone methyltransferase EZH2 inhibitor is 3-Deazaneplanocin A (DZNep).

3. The method according to claim 1, wherein the TGF-beta signaling pathway inhibitor is Alk5iII.

4. The method according to claim 1, wherein the medium in step (1) further comprises one or more additional agents selected from group consisting of a gamma-secretase inhibitor, a cAMP-elevating agent, a thyroid hormone signaling pathway activator, and combinations thereof.

5. The method according to claim 4, wherein the gamma-secretase inhibitor is DAPT.

6. The method according to claim 4, wherein the thyroid hormone signaling pathway activator is T3.

7. The method according to claim 1, wherein the histone methyltransferase EZH2 inhibitor is 3-Deazaneplanocin A (DZNep), and wherein the TGF-beta signaling pathway inhibitor is Alk5iII.

8. The method according to claim 1, wherein the histone methyltransferase EZH2 inhibitor is 3-Deazaneplanocin A (DZNep), wherein the TGF-beta signaling pathway inhibitor is Alk5iII, and wherein step (1) further comprises T3.

9. A method for generating INS+ and NKX6.1+ double positive immature beta cells from endocrine progenitor cells, comprising culturing the endocrine progenitor cells in a basal medium comprising a histone methyltransferase EZH2 inhibitor, a TGF-beta signaling pathway inhibitor, Heparin, and Nicotinamide; wherein the endocrine progenitor cells are differentiated from pancreatic endoderm cells.

10. The method according to claim 9, wherein the histone methyltransferase EZH2 inhibitor is 3-Deazaneplanocin A (DZNep).

11. The method according to claim 9, wherein the TGF-beta signaling pathway inhibitor is Alk5iII.

12. The method according to claim 9, wherein the histone methyltransferase EZH2 inhibitor is 3-Deazaneplanocin A (DZNep), and wherein the TGF-beta signaling pathway inhibitor is Alk5iII.

13. The method according to claim 9, further comprising culturing the stem cell-derived endocrine progenitor cells in a basal medium comprising T3.

14. The method according to claim 9, wherein the histone methyltransferase EZH2 inhibitor is 3-Deazaneplanocin A (DZNep), wherein the TGF-beta signaling pathway inhibitor is Alk5iII, and wherein the method further comprises culturing the stem cell-derived endocrine progenitor cells in a basal medium comprising T3.

\* \* \* \* \*

UNITED STATES PATENT AND TRADEMARK OFFICE
CERTIFICATE OF CORRECTION

| | |
|---|---|
| PATENT NO. | : 11,274,280 B2 |
| APPLICATION NO. | : 16/078763 |
| DATED | : March 15, 2022 |
| INVENTOR(S) | : Christophersen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 407 days.

Signed and Sealed this
Thirteenth Day of December, 2022

Katherine Kelly Vidal
*Director of the United States Patent and Trademark Office*